US005587402A

United States Patent [19]

Gould et al.

[11] Patent Number: 5,587,402
[45] Date of Patent: Dec. 24, 1996

[54] REGRESSION OF MAMMALIAN LEUKEMIA CELL TUMORS

[75] Inventors: Michael N. Gould, Madison, Wis.; Pamela L. Crowell, Indianapolis, Ind.; Charles E. Elson; Steven S. Clark, both of Madison, Wis.

[73] Assignee: Wisconsin Alumni Research Foundation, Madison, Wis.

[21] Appl. No.: 434,811

[22] Filed: May 4, 1995

Related U.S. Application Data

[63] Continuation-in-part of Ser. No. 865,561, Apr. 9, 1992, Pat. No. 5,414,019.
[51] Int. Cl.$^6$ .................................................. A61K 31/045
[52] U.S. Cl. .................................................. 514/729
[58] Field of Search .................................................. 514/729

[56] References Cited

U.S. PATENT DOCUMENTS

| 5,110,832 | 5/1992 | Chastain | 514/729 |
| 5,244,916 | 9/1993 | Bokoch | 514/460 |

OTHER PUBLICATIONS

Elegbede, et al., "Inhibition of DMBA-induced Mammary Cancer By the Monoterpene D–Limonene,"*Carcinogenesis*, 5[5]:661–664, (1984).
Elegbede, et al., "Regression of Rat Primary Mammary Tumors Following Dietary d–Limonene," *JNCI*, 76[2]:323–325 (1986).
Haag, et al., "Limonene–induced Complete Regression of Rat Mammary Carcinomas," *Proc. Of The Amer. Assoc. For Cancer Research*, 32:402 Abs #2391 (1991).
Elson, et al., "Anti-carcinogenic Activity of d–limonene During the Initiation And Promotion/Progression Stages of DMBA–induced Rat Mammary Carcinogenesis," *Carcinogenesis*, 9[2]331:332 (1988).
Maltzman, et al., "The Prevention of Nitrosomethylurea–induced Mammary Tumors by d–Limonene and Orange Oil,", *Carcinogenesis*, 10[4]:781–783 (1989).
Wattenberg, et al., "Inhibition Of 4–(Methylnitrosamino)–1–(3–pyridyl)–1–Butanone Carcinogenesis In Mice By D–limonene And Citrus Fruit Oils," *Carcinogenesis*, 12[1]:115–117 (1991).
Van Duuren, et al., "Cocarcinogenic And Tumor–Promoting Agents In Tabacco Carcinogenesis," *Journ. of the Natl. Cancer Institute*, 56[6]:1237–1242 (1976).
Homburger, et al., "Inhibition of Murine Subcutaneous And Intraveneous Benzo(rst)pentaphene Carcinogensis By Sweet Orange Oils and D–Limonene," *Oncology*, 25:1–10 (1971).
Crowell, et al., "Selective Inhibition Of Isoprenylation Of 21–26kDa Proteins By The Anticarcinogen d–Limonene And Its Metabolites," *The Journ. of Biol. Chem.*, 266[26]:17679–17685 (Sep. 1991).
Gould, "Chemoprevention And Treatment Of Experimental Mammary Cancers By Limonene," *Proc. of the Amer. Assoc. For Cancer Res.*, 32:474–475 (1991).

Abtract 3134, Crowell, et al., "Human Metabolism of Orally Adminstered D–Limonene," *Proc. Of the Amer. Assoc. For Cancer Research*, 33:524 (1992) (see also 3135).
Crowell, et al., "Identification of Metabolites of the Antitumor Agent d–limonen Capable of Inhibiting Protein Isoprenylation and Cell Growth," *Cancer Chemotherapy and Pharmacology*, 31:205–212, 1992.
Crowell, et al., "Chemoprevention of Mammary Carcinogenesis By Hydroxylated Derivative of d–limonene," *Carcinogenesis*, 13(7):1261–1264 (1992).
Haag, et al., "Limonene–induced Regression of Mammary Carcinomas," *Cancer Research*, 52:4021–4026 (1992).
Ren, et al., "Inihibition of Ubiquinone and Cholesterol Synthesis by the Monoterpene Perillyl Alcohol," *Cancer Letters*, 76:185–190 (1994).
W. Shi, et al., "Differentiation of Neuro–2a Cells Induced by the Monoterpene, Perillyl Alcohol (POH)," *Proc. Of The Amer. Assoc. For Cancer Research*, 34:548 (1993).
Ren, et al., "Inhibition of Ubiquinone Biosynthesis by the Monoterpene Perillyl Alcohol (POH)," *Proc. Of The Amer. Assoc. For Cancer Research*, 34:548 (1993).
Plenary Session 4: Mechanisms of action of chemopreventive agents: Basic science and clinical applications, Gould, et al., "Chemoprevention of mammary cancer by monoterpenes," *Proceedings*, Eighty–Fourth annual Meeting, American Association for Cancer Research p. 572–73, vol. 34 (1993).
Gould, et al., Proposal, "Phase I Evaluation of Perillyl Alcohol (NSC 641066) in Patients With Cancer," distributed in Aug., 1993.
Gould, et al., "Perillyl Alcohol (NSC 641066) Summary of Activities in the Development Therapeutics Program, DCT, NCI," distributed in Feb., 1994.
Gould, et al., "Perillyl Alcohol (NSC 641066) and Limonene (NSC 844) Summary for the Decision Network," distributed in Feb., 1994.
Crowell, et al., "Structure–Activity Relationships Among Monoterpene Inhibitors of Protein Isoprenylation and Cell Proliferation," *Biochemical Pharmacology*, 47:14–15, 1994.
Gould, et al., "Cellular and Molecular Aspects of the Multistage Progression of Mammary Carcinogenesis in Humans and Rats," *Cancer Biology*, 4;161–169 (1993).
Clark, et al., "Molecular Pathogenesis of Ph–Positive Leukemias," *Ann. Rev. Med.*, 40:113–22 (1989).
Abstract 3135, Haag, et al., Proceedings of the Eighty–Third Annual Meeting of the American Association for Cancer Research, vol. 33, p. 524, Mar. 1992.
Ren, et al., "Inhibition of ubiquinone and cholesterol synthesis by the monoterpene perillyl alcohol," *Cancer Letters* 2[3]:185–190, 1994.
Bronfen, et al., "Inhibition of human pancreatic carcinoma cell proliferation by perillyl alcohol," *Proc. Annu. Meet. Am. Assoc. Cancer Research* 35:431, 1994.
Crowell, et al., "Structure–activity relationships among monoterpene inhibitors of protein isoprenylation and cell proliferation," *Biochem. Pharmacol.* 47 [8]:1405–1415, 1994.

*Primary Examiner*—Jerome D. Goldberg
*Attorney, Agent, or Firm*—Quarles & Brady

[57] ABSTRACT

A method for causing regression of a leukemia cell tumor is disclosed. This method comprises the step of administering perillyl alcohol to a tumor-containing mammal.

3 Claims, 17 Drawing Sheets

C, NO MONOTERPENE CONTROL

5PA, 5mM PERILLIC ACID

1POH, 1mM PERILLYL ALCOHOL

3POH, 3mM PERILLYL ALCOHOL

EQUAL AMOUNTS OF TOTAL CELLULAR PROTEIN WERE LOADED ONTO EACH LANE OF THE GEL.

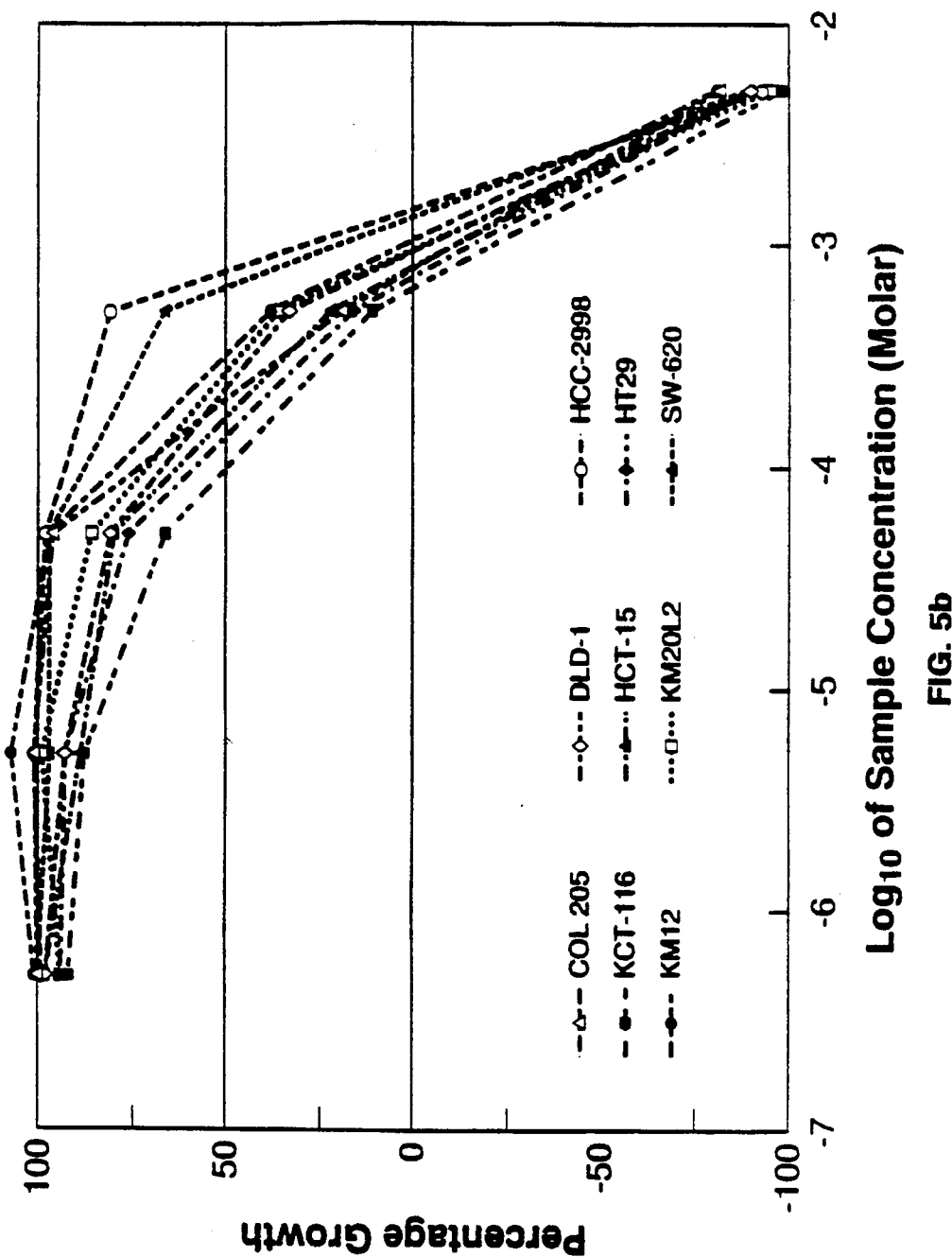

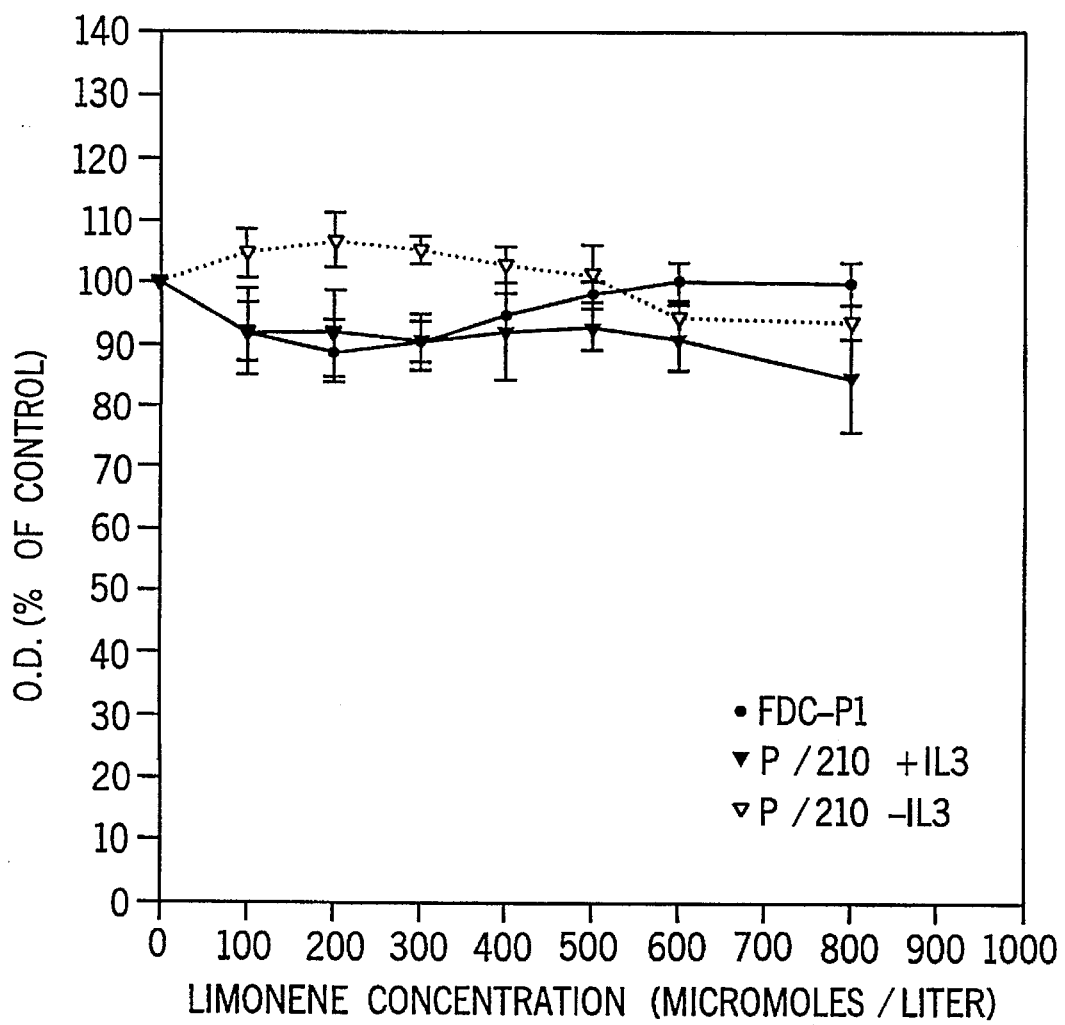

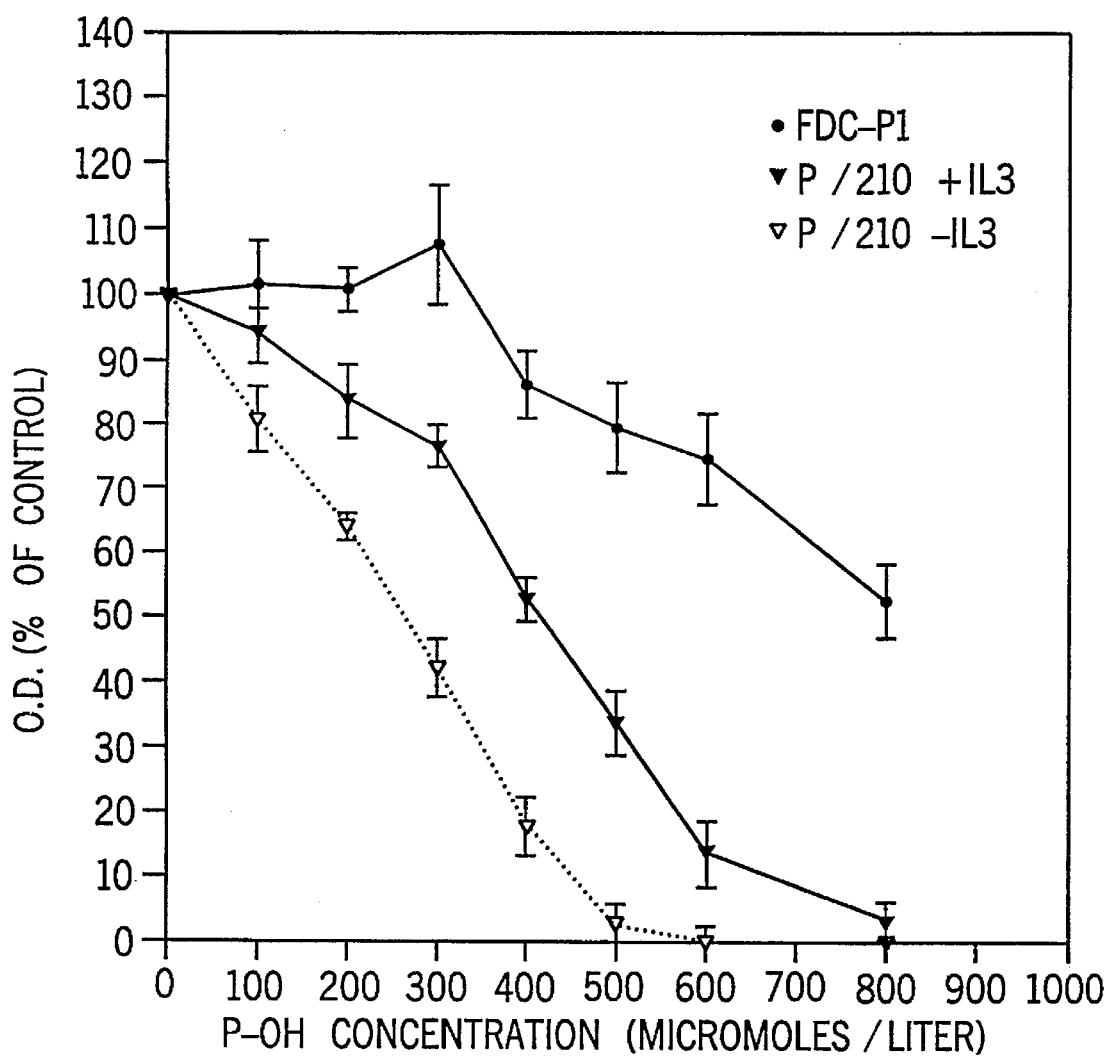

REGRESSION OF MAMMALIAN LEUKEMIA CELL TUMORS

RELATED APPLICATION

This application is a continuation-in-part of U.S. Ser. No. 07/865,561, filed Apr. 9, 1992, now U.S. Pat. No. 5,414,019, which is incorporated by reference as if fully set forth herein.

TECHNICAL FIELD

The present invention relates to treatments for mammalian leukemia cell tumors. In particular, the present invention relates to the use of certain oxygenated (preferably hydroxylated) monoterpenes to inhibit tumor formation and cause tumor regression.

BACKGROUND

Limonene is a monoterpene that is present in orange peel oil and has been reported to have activity against mammary (Elegbede, et al., 1984, Carcinogenesis 5: 661–664; Elegbede, et al., 1986, J. Natl. Cancer Inst. 76: 323–325; Haag, et al., 1991, Proc. Am. Assoc. Cancer Res. 32: 402); Elson, et al., 1988, Carcinogenesis 9: 331–332; Maltzman, et. al., 1989, Carcinogenesis 10: 781–783), lung, and stomach (Wattenberg, et al., 1991, Carcinogenesis 12: 115–117) cancers. (These references and all others cited herein are hereby incorporated by reference as if fully set forth herein.) Limonene has also been shown to inhibit certain skin tumors. Van Duuren et al., 1976, J. Natl. Cancer Inst., 56: 1237–1242; F. Homburger et al., 1971, Oncology, 25: 1–20.

Although studies have shown that limonene is not toxic to humans at the required usage levels, treatment with limonene is not without some side-effects, particularly when a large dose of limonene is required in a short period.

SUMMARY OF THE INVENTION

The present invention provides methods for causing regression and inhibition of leukemia cell tumors in mammals. In one aspect, one administers to a leukemia cell tumor-containing mammal an effective amount of perillyl alcohol. In an especially preferred embodiment, the tumor is Ph(+).

One object of the present invention is to cause the regression of leukemia cell tumors.

Another object of the present invention is to prevent a reoccurance of leukemia cell tumors in patients that have already been treated for primary leukemia and entered remission.

Another object of the present invention is to inhibit mammalian leukemias that carry the Philadelphia ("Ph(+)") chromosome.

Other objects, advantages and features of the present invention will become apparent upon examination of the specification, drawings and claims.

BRIEF DESCRIPTION OF THE DRAWINGS

FIGS. 9A and B are diagrams of cell proliferation versus limonene and perillyl alcohol concentration for p210 transformed FDC-P1 cells and control cells.

DESCRIPTION OF THE PREFERRED EMBODIMENTS

SPECIFIC EXAMPLES

Figure 1:
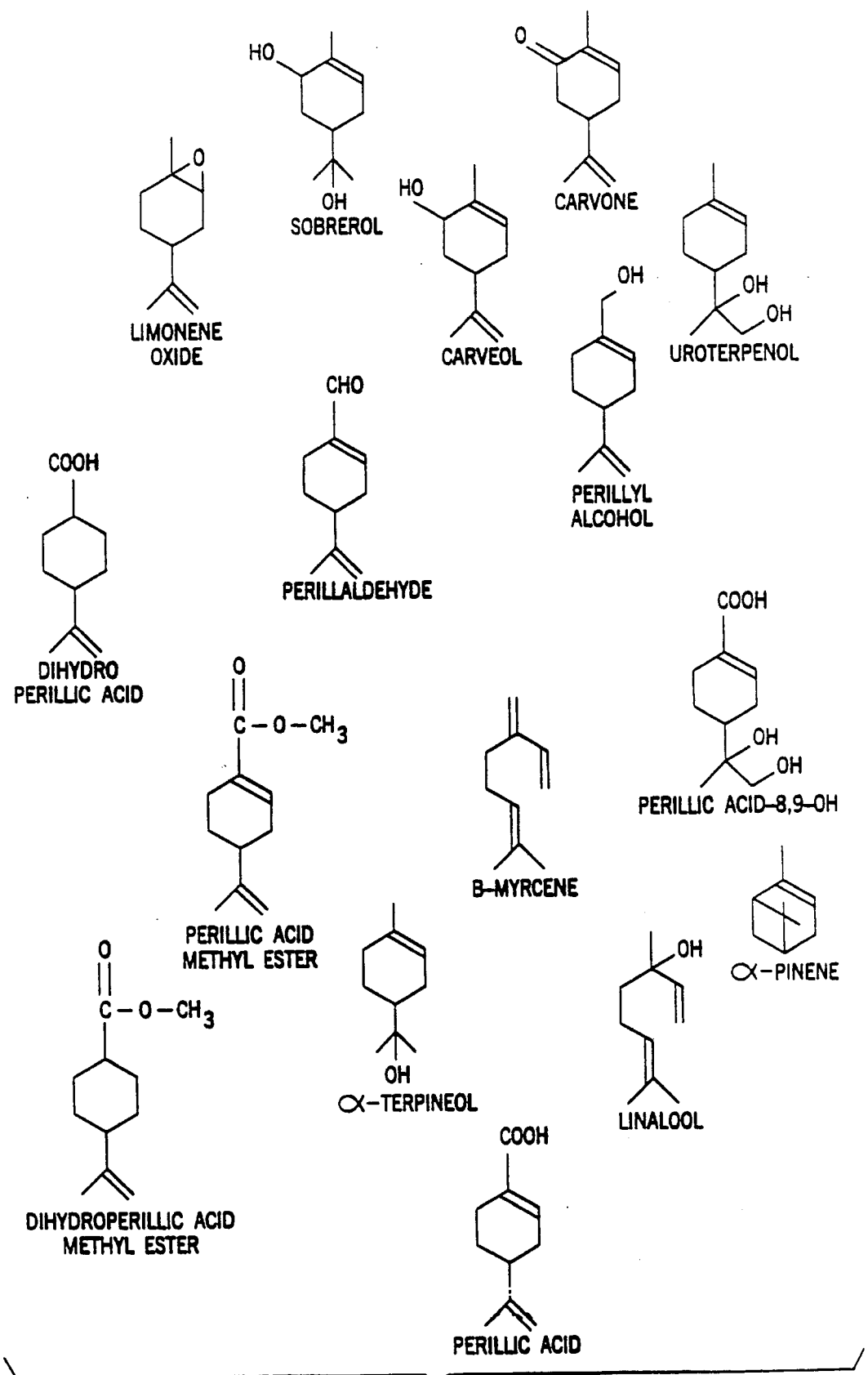
FIG. 1 is a diagram of the chemical structure of 16 monoterpenes.

The present invention is a method of causing the inhibition or regression of leukemia cell tumors. By "leukemia cell tumor" we mean a condition in which a mammalian patient has a malignant proliferation of hematopoietic cells. We mean "leukemia cell tumor" to be synonymous with hematopoietic malignancies or hematopoietic tumors.

Examples 1–3 describe the characterization of perillyl alcohol as a chemotherapeutic and tumor regression agent. These examples include a demonstration of the efficacy of perillyl alcohol on several types of leukemia cells. Examples 4 and 5 focus on Ph$^+$ leukemias. Example 4 describes the use of perillyl alcohol to inhibit proliferation of bcr/abl transformed murine FDC-P1 myeloid cells in vitro. Example 5 describes the effects of perillyl alcohol on bcr/abl-induced leukemia in mice.

1. Biological Activity a. Cell Culture and Strains

NIH3T3 (mouse embryo) cells were obtained from the American Type Culture Collection and were grown in Dulbecco's modified Eagle's medium supplemented with 10% calf serum. M600B immortalized human mammary epithelial cells (Stampfer, M. R., 1985, J. Tissue Culture Methods 9: 107–115) were obtained from Dr. Martha Stampfer and were grown in supplemented HCDB 170 medium (Hammond, et al. (1984) Proc. Natl. Acad. Sci U.S.A. 81: 5435–5439), as described previously (Stampfer, et al. (1985) Proc. Natl. Acad. Sci U.S.A. 82: 2394–2398; Eldridge, et al. (1989) Cancer Res. 49: 4326–4331).

All cells were maintained in 100-mm dishes at 37° C. in a humidified 5% $CO_2$ atmosphere. Viable cells were distinguished from nonviable cells by counting azure II/methylene blue-stained colonies 10 days after the cells were plated at a density of 100 cells per dish. Trypan blue exclusion was measured by incubating cells for 1 minute with one drop of trypan blue per 10 ml of cells. Viable (colorless) and nonviable (blue) cells were then counted on a hemocytometer.

b. Measurement of Protein Isoprenylation

"Isoprenylation" is the addition of a multiple of the 5 carbon isoprene unit to a protein. Our experiments in isoprenylation are reported at Crowell, et al. 1991, J. Biol. Chem. 266: 17679–17685. To test whether a specific monoterpene affects isoprenylation of proteins in cells, cell extracts were incubated with a radioactive isoprene precursor and 0–5 mM of the test monoterpene and then subjected to SDS-PAGE. Because they carried a radioactive label, isoprenylated proteins were visualized by fluorography. As a control, cells were incubated without the monoterpene.

Isoprenylation of proteins was measured essentially as described by Schmidt et al., 1984, *J. Biol. Chem.* 259: 10175–10180. In brief, cells were treated with 30 μM lovastatin for 24 hours and then incubated for 3 hours in fresh medium containing 15 μCi/mL (R,S) - [2-14C]mevalonolactone (50 mCi/mmol), 30 μM lovastatin, and, where indicated,-a test monoterpene. For both isoprenylation and cell growth assays, the monoterpenes were mixed with prewarmed (37°) medium containing 10% calf serum, and then the monoterpene-containing medium was added to cells. The relative effects of various monoterpenes on protein isoprenylation were compared by comparison of the relative intensity of bands on fluorograms from [14C]-mevalonate-labelled cells treated with each monoterpene. 10% calf serum was included in the normally serum-free HCDB 170 medium of control and limonene-treated M600B cells during the 3 hours incubation to solubilize limonene.

Cells were harvested after trypsin treatment, washed twice with phosphate-buffered saline, suspended in electrophoresis sample buffer (Laemmli, U.K., 1970, *Nature* 227: 680–685), and either analyzed immediately or stored at –20° C. Whole cell extracts were analyzed by SDS-PAGE on 16-cm×18-cm×0.75-mm gels by the method of Laemmli (supra). The acrylamide concentrations were 5% for the stacking gel and 12% for the separating gel. Gels were stained with Coomassie Brilliant Blue, equilibrated for 20 minutes in Amplify (Amersham Corp.) fluorographic reagent, dried under vacuum at 65° C., and exposed to preflashed Kodak X-Omat AR film as described by Laskey and Mills (1975, *Eur. J. Biochem,* 56: 335–341). Some fluorograms were analyzed further by densitometry. Where indicated, gels were sliced, dissolved at 50° C. for 3 hours in 0.5 ml of water +0.5 ml of Solvable (Amersham), and then analyzed by scintillation spectrometry in 10 ml of Atomlight (Amersham) mixture. Protein content was measured by the method of Lowry, et al. (1951, *J. Biol. Chem.* 193: 265–275).

As reported in Crowell, et al. (supra) radioactivity derived from [2–14C]mevalonolactone was detected in control cells in bands corresponding to molecular masses of 66, 46, 21–26, and 17 kDa, as well as at the dye front. Cells treated with 0.5 mM or 5 mM limonene exhibited a dose-responsive decrease in intensity of the 21–26-kDa bands. The spot at the dye front was reduced with maximal inhibition at 5 mM (the limit of solubility). The intensity of the 66-, 46-, and 17-kDa bands from the limonene-treated cells was not different from that of the control. Slicing and scintillation counting of a duplicate gel revealed that limonene inhibited isoprenylation of the 21–26-kDa bands to ~50% of the control at 0.5 mM and ~25% of the control at 5 mM.

c. Test Panel of Monoterpenes in NIH3T3 Cells

The monoterpenes listed in Table 1 were analyzed as described above for their ability to differentially inhibit isoprenylation in NIH3T3 (mouse embryo) cells. FIG. 1 depicts the structures of these monoterpenes. Limonene was tested at a concentration of 5 mM; all other terpenes were tested at a concentration of 1 mM.

The degree of isoprenylation was evaluated by the amount of labeled protein present in the 21–26 kDa range, as evidenced by fluorography. These results were quantitated according to the intensity of the radioactive image. The symbol +++++ denotes the least amount of radioactive material in the 21–26 kDa range and, therefore, the most ability to inhibit isoprenylation. As with limonene, the monoterpenes differentially inhibited isoprenylation. Therefore, isoprenylation of the 21–26 kDa proteins was inhibited but the isoprenylation of other proteins remained unchanged.

TABLE 1

| Compound | Relative activity |
|---|---|
| Experiment 1 | |
| d-Limonene | + |
| Limonene oxide (limonene 1,2-epoxide) | – |
| Sobrerol (trans-p-menth-6-ene-2,8-diol) | ++ |
| Perillic acid | ++ |
| Perillic acid methyl ester | – |
| Dihydroperillic acid | ++ |
| Dihydroperillic acid methyl ester | – |
| B-myrcene | – |
| α-pinene | – |
| Perillaldehyde | ++ |
| Carvone | – |
| Experiment 2 | |
| d-Limbonene | + |
| Perillyl alcohol | +++++ |
| Perillaldehyde | ++ |
| Perillic acid | ++ |
| Perillic acid-8,9-OH | ++ |
| Uroterpenol | ++ |
| Carveol | +++ |
| α-Terpineol | ++++ |
| Linalool | ++++ |
| Sobrerol (trans-p-menth-6-ene-2,8-diol) | +++ | d. Inhibition of Protein Isoprenylation in M600B Human Cells

The ability of limonene to inhibit isoprenylation of proteins was tested in the immortalized human mammary epithelial cell line M600B. Protein isoprenylation in the absence and presence of 5 mM limonene was measured under identical conditions in NIH3T3 and M600B cells. Samples from each cell line were then analyzed on the same gel. The control mammary epithelial cells exhibited the ability to isoprenylate proteins of 23–26 kDa. Other bands, corresponding to molecular masses of 72, 66, 46, and 17 kDa, could be detected in the mammary epithelial cells after longer exposures. The intensity of the 21–26 kDa bands from untreated cells was much greater for the mammary epithelial cell line than the NIH3T3 cell line.

As in the NIH3T3 cells, M600B cells treated with 5 mM limonene exhibited a marked decrease in the intensity of the 21–26 kDa bands. The effect was dose responsive, with at least 1 mM limonene required for significant inhibition of protein isoprenylation.

Figure 2:
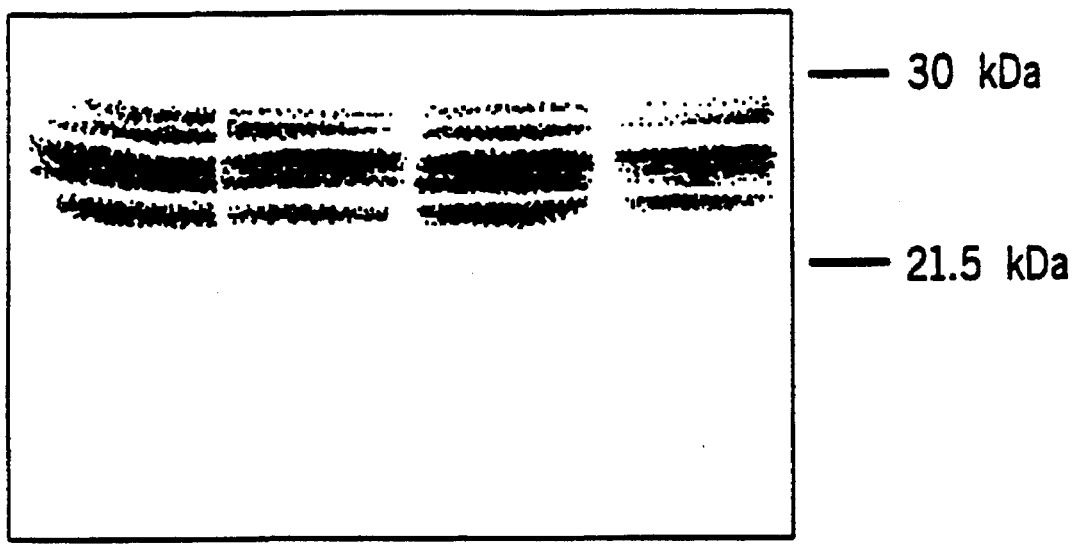
FIG. 2 is a fluorogram revealing the effects of perillic acid and perillyl alcohol on isoprenylation of proteins in M600B human cells.

As in NIH3T3 cells, isoprenylation of 21–26 kDa proteins in M600B human mammary epithelial cells was inhibited significantly by 3 mM perillyl alcohol and 5 mM perillic acid. FIG. 2 is a copy of a fluorogram that demonstrates these results. This experiment also illustrated the ability of these methods to detect various degrees of inhibition of protein isoprenylation.

The relative inhibition by terpenes varies slightly between cell types, but in all cases we have examined, inhibition of isoprenylation by perillic acid and perillyl alcohol was observed.

e. Inhibition of Cell Growth

Figure 3:
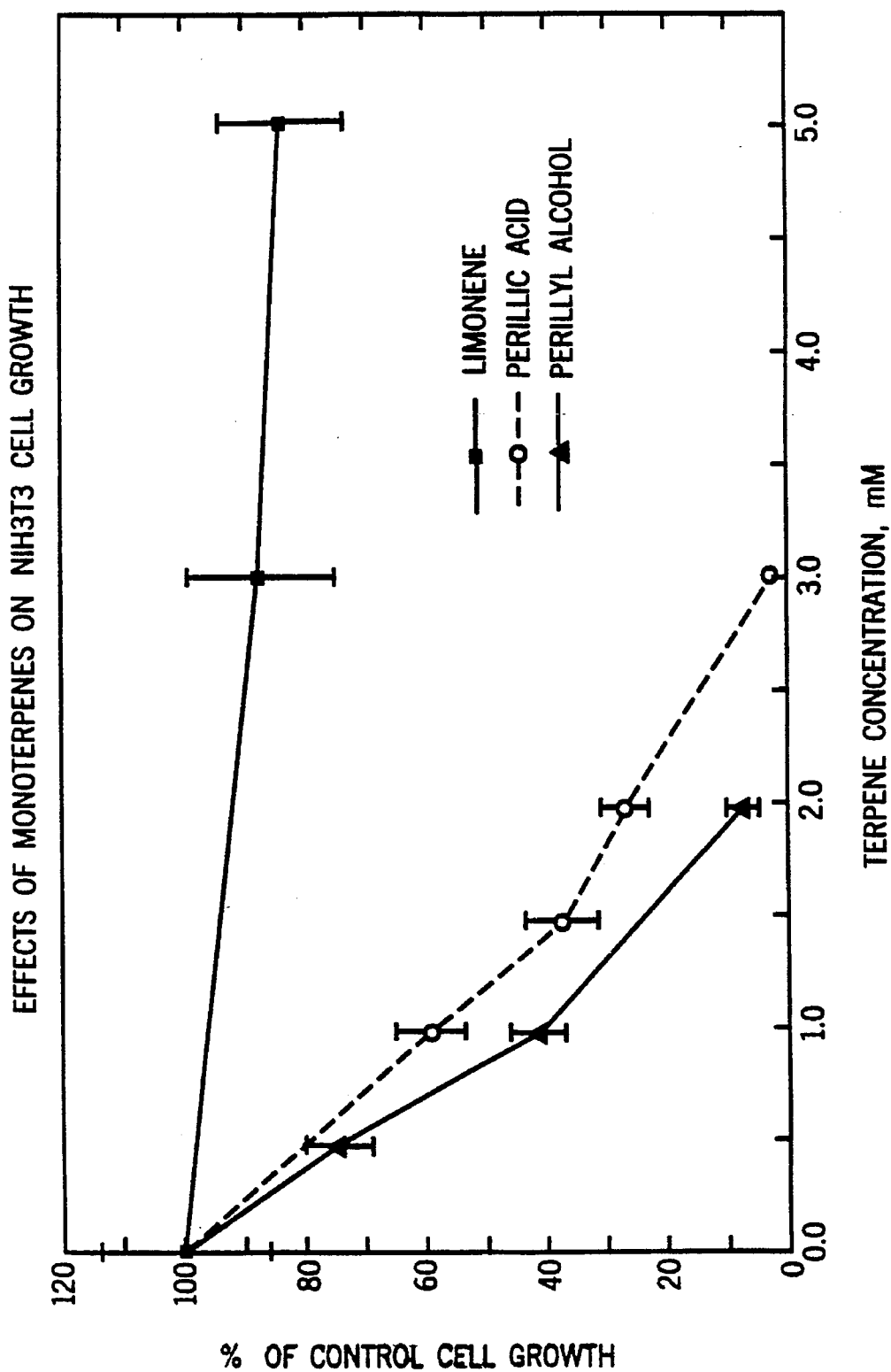
FIG. 3 is a diagram of the effect of limonene, perillic acid and perillyl alcohol on NIH3T3 cell growth.
Figure 4:
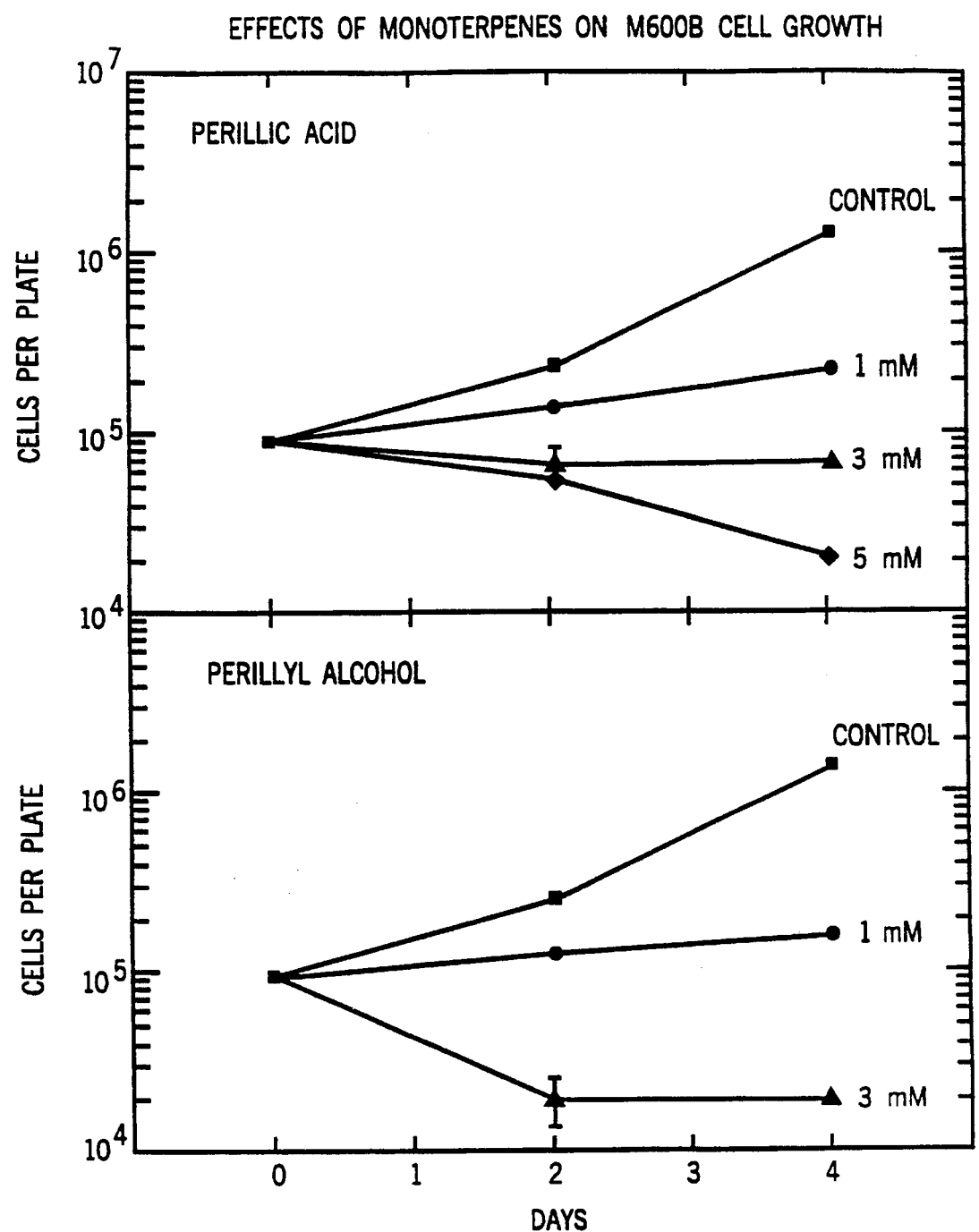
FIG. 4 is a diagram of the effect of perillic acid and perillyl alcohol on M600B cell growth.

Since many of the 21–26 kDa isoprenylated proteins have an implicated or demonstrated role in signal transduction and growth control, we hypothesized that compounds capable of inhibiting isoprenylation would also inhibit cell growth. For the human and murine cells, both perillic acid and perillyl alcohol significantly inhibited cell growth in a dose-dependent manner (FIGS. 3 and 4, respectively). Additionally, growth of HT29 (human colon adenocarcinoma) cells was inhibited by 80% by 1 mM perillyl alcohol.

Various concentrations of perillyl alcohol inhibited the growth of a number of human cancer cell lines. FIG. 5A–G is a set of diagrams showing the effects of perillyl alcohol on different cancer cell lines. These experiments were conducted by the National Cancer Institute Developmental Therapeutics Program. In all cases, perillyl alcohol inhibited cancer cell growth.

2. The Effects of Dietary Perillyl Alcohol on Tumor Regression and Inhibition in Wistar-Furth Rats a. Tumor Induction We used Wistar-Furth female rats for in vivo studies. Wistar-Furth female rats were obtained from Harlan Sprague-Dawley, Inc., (Madison, Wis.). All rats, arriving at 43–48 days of age, were housed at four rats per cage in wire-bottom metal cages and all were maintained with a light/dark cycle of 12 hours. Rates were provided Teklad Lab blox chow and acidified water ad libitum.

After one week of acclimation, the carcinogen DMBA was administered to the rats, which were 50–55 days old at this point. The DMBA was dissolved in a stock solution of 20 mg DMBA/ml sesame oil, heated and allowed to cool to room temperature before administration. DMBA (Eastman Kodak, Rochester, N.Y.) was given as a single gastric intubation of 50 mg DMBA/kg rat body weight.

b. Monoterpene Administration

In the pair-feeding study, a group of 70 mammals was treated with DMBA. Beginning four weeks post-carcinogen administration, mammals were weighed and palpated weekly. Upon palpation of the first mammary tumor(s) (diameter$\geq$3 mm), mammals were randomly assigned to control or 2.5% (w/w) perillyl alcohol diet and pair-fed. In a separate experiment, mammals were assigned control or 10% (w/w) limonene diet and pair fed.

Perillyl alcohol (>96% pure by GC analysis, Aldrich, Milwaukee, Wis.) and Teklad 4% mouse/rat diet meal were thoroughly mixed and stored at −20° C. Fresh diets were make every 7–10 days. All mammals were provided fresh diet daily to minimize evaporation of the monoterpenes. For pair-feeding, the quantity of diet consumed by the monoterpene-fed mammals was measured every 24 hours and the assigned partner was pair-fed accordingly.

c. Tumor Regression Evaluation

In a pair-feeding study, all palpable mammary tumors were classified as either "primary" tumors (i.e., the first tumor(s) palpated with a minimum diameter of 3 mm) or "secondary" tumors (i.e. a palpable tumor arising after initial diet assignment). At diet assignment, some mammals had more than one primary tumor. All carcinogen-exposed mammals not bearing a first palpable tumor by week 15 post-carcinogen were removed from the experiment. Complete regression of a tumor was defined as non-palpability for a minimum of three consecutive weeks. All mammals in the pair-feeding study were followed for a minimum of 10 weeks post-diet assignment for tumor growth or regression at primary tumor sites and all other mammary glands. The rats were necropsied if moribund. Complete necropsies were performed on all rats at the termination of the study. Greater than 95% of tumors remaining at the autopsy date were diagnosed as mammary carcinomas based on gross and histopathological criteria.

d. Results of the Pair-Feeding Study

DMBA-treated mammals were assigned to perillyl alcohol or limonene diet at an average of 10.4 weeks ±0.5 (mean ±SEM). At the time of diet assignment, the average tumor diameter was 4.4 mm ±0.2. Mammals were assigned to the control group 10.1 weeks ±0.5 post-DMBA treatment. Their average tumor diameter at diet assignment was 3.9 mm ±0.2.

Figure 6:
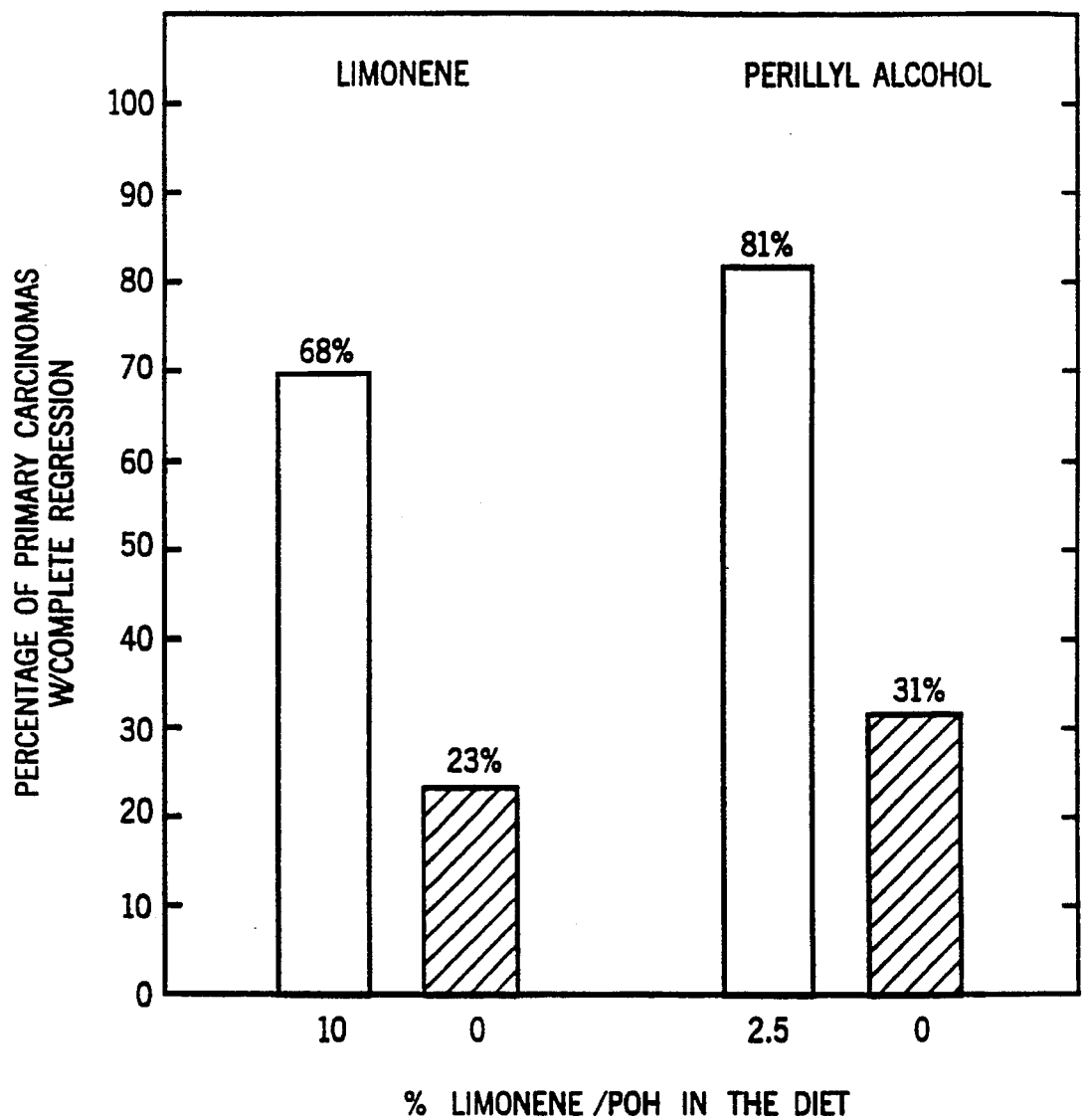
FIG. 6 is a bar graph comparing the effects of a 10% limonene diet and a 2.5% perillyl alcohol diet in the regression of mammary tumors.

Table 2 and FIG. 6 disclose the results of these experiments. DMBA-induced primary carcinomas in perillyl alcohol-treated mammals had a complete regression rate of 81% (22 tumors out of 27) compared with 31% (9 tumors out of 29) for pair-fed controls. DMBA-induced primary carcinomas in limonene-treated mammals had a complete regression rate of 68% (19 tumors out of 28) compared with a rate of 23% (6 tumors out of 26) for pair fed controls. We therefore noted that the amount of perillyl alcohol needed to achieve these results was 25% the amount of limonene needed. The time required for a primary tumor to regress to a non-palpable mass in the perillyl alcohol-treated group was shorter than the time for spontaneous regression in the pair-fed controls. (3.6 wks ±0.3 versus 5.6 wks ±1.1).

e. Inhibition of Tumorigenesis

Figure 7:
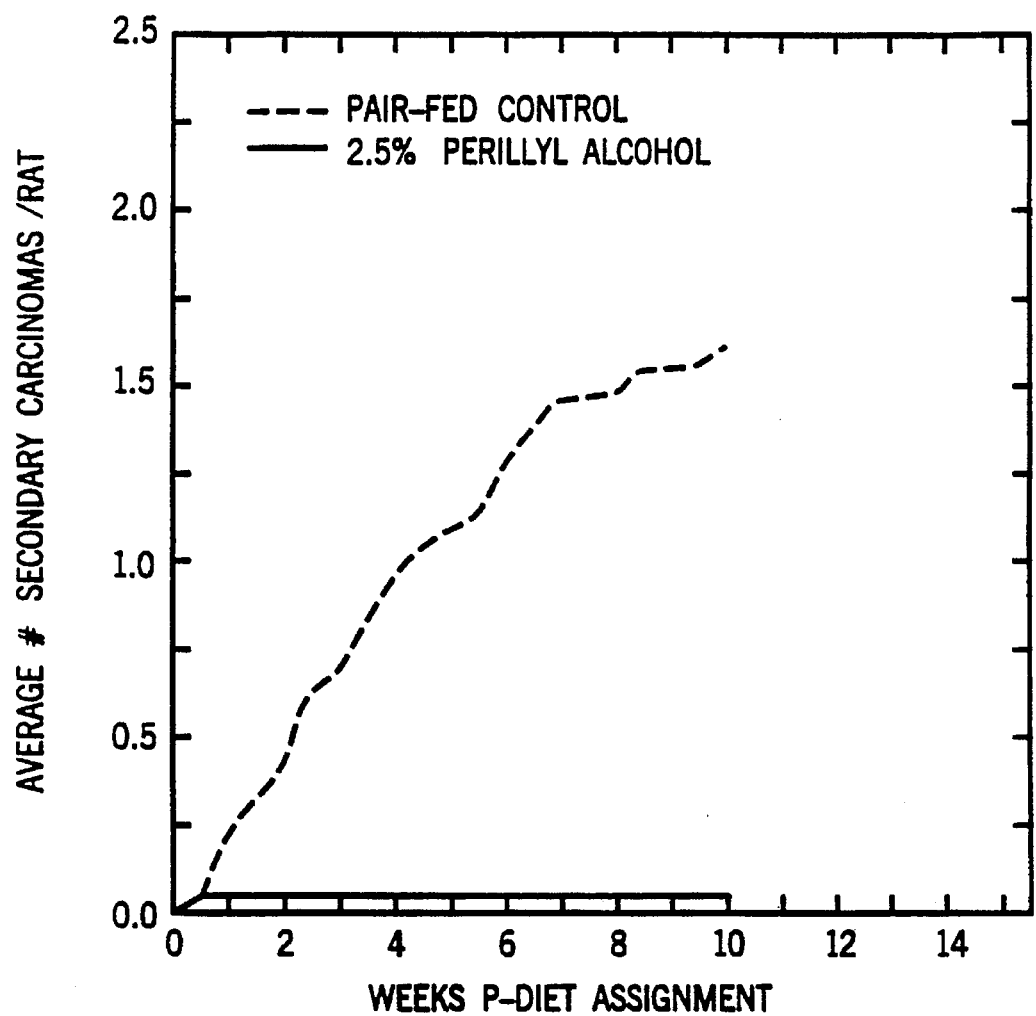
FIG. 7 is a diagram comparing the average number of secondary mammary tumors in mammals fed 2.5% perillyl alcohol and in pair-fed controls.

Perillyl alcohol also inhibited the development of secondary tumors arising after initial diet assignment. The average number of secondary tumors/mammal for mammals consuming 2.5% perillyl alcohol diet was 0.04 (1/26) as compared to 1.62 (42/26) for pair-fed controls. Table 2 discloses that the number of secondary tumors was higher in the limonene-fed mammals than in the mammals that were fed perillyl alcohol. FIG. 7 is a diagram comparing secondary tumors in perillyl alcohol-fed animals and controls.

TABLE 2

Complete regression of DMBA = induced rat mammary carcinomas by dietary limonene and perillyl alcohol.

| DMBA | Rats (n) | Primary Tumor Regression (%) | **Time to Regress (wks) | Number of Secondary Tumors/Rat | Secondary Tumor Regression (%) |
|---|---|---|---|---|---|
| 10% limonene diet | 25 | *19/28 (68) | *3.25 | *1.08 | *17/27 (63) |
| Pair-fed control | 25 | 6/26 (23) | 14.5 | 1.92 | 9/48 (19) |
| DMBA | | | | | |
| 2.5% POH diet | 26 | 22/27 (81) | 3.6 + 0.3 | 0.04 | 0/1 (0) |
| Pair-fed control | 26 | 9/29 (31) | 5.6 + 1.1 | 1.62 | 11/42 (26) |

*Significantly different than controls ($p < 0.01$).
**Kaplan-Meier estimate of the time when 25% of tumors will have regressed.

f. Toxicity

Figure 8:
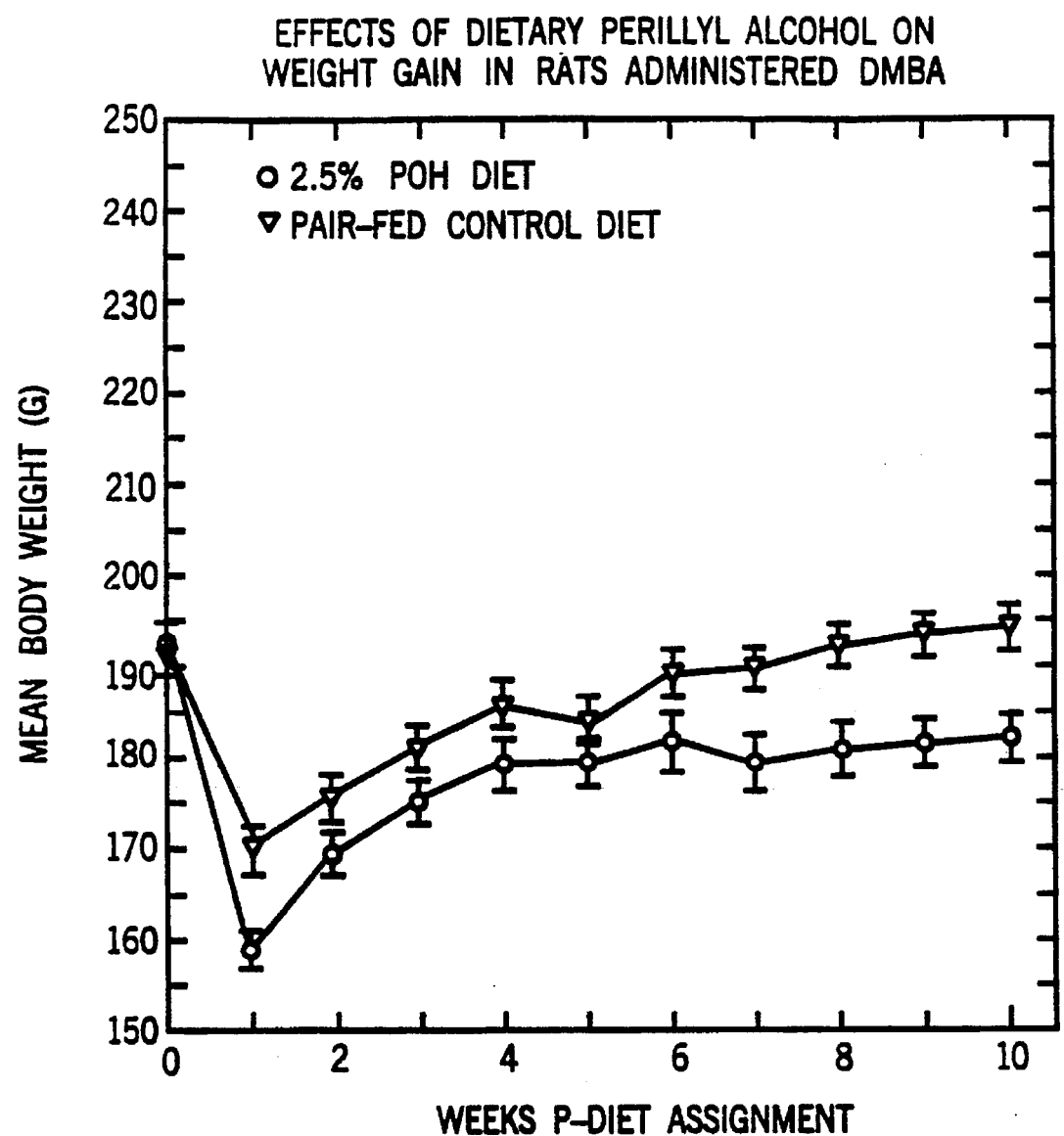
FIG. 8 is a diagram of the effect of perillyl alcohol on mammal weight gain.

Toxicity was limited to weight loss in perillyl alcohol-fed rats. FIG. 8 diagrams these results. Both perillyl alcohol-fed and control mammals experienced initial weight loss followed by weight gain and a plateau. The perillyl alcohol-fed rats did not achieve weights similar to controls. In toxicity studies (data not shown), 2.5% perillyl alcohol diet was the maximum dose tolerated by the animals.

g. Screening of Additional Monoterpenes

Other compounds may be screened, as above, for their efficacy as a treatment against tumors. The compound will first be tested for its ability to differentially prevent isoprenylation of proteins. Most preferably this assay will take place in either NIH3T3 cells or M600B human mammary epithelial cells. Our experiments above demonstrate that a inhibition of isoprenylation of proteins of approximately 21–26 kDa and a lack of inhibition of isoprenylation of other cellular proteins is an indication of a compound's efficacy in treating tumors. The test results in NIH3T3 cells may be compared with FIG. 8 in Crowell, et al. (supra.). A differential inhibition of isoprenylation as great as that shown for perillic acid and perillyl alcohol indicates that the compound is a candidate for a chemotherapeutic.

Although NIH3T3 cells and mammary epithelial cells are preferred test hosts, other cells types would also be effective hosts. We have performed the same isoprenylation inhibition studies with HT29, a human colon adenocarcinoma cell line available from ATCC, with perillyl alcohol and achieved similar differential isoprenylation results. In HT29 cells, 1 mM perillyl alcohol decreased isoprenylation of 21–26 kDa proteins by 40%.

3. Use as a Chemotherapeutic a. Other Tumor Types

Figure 5A:
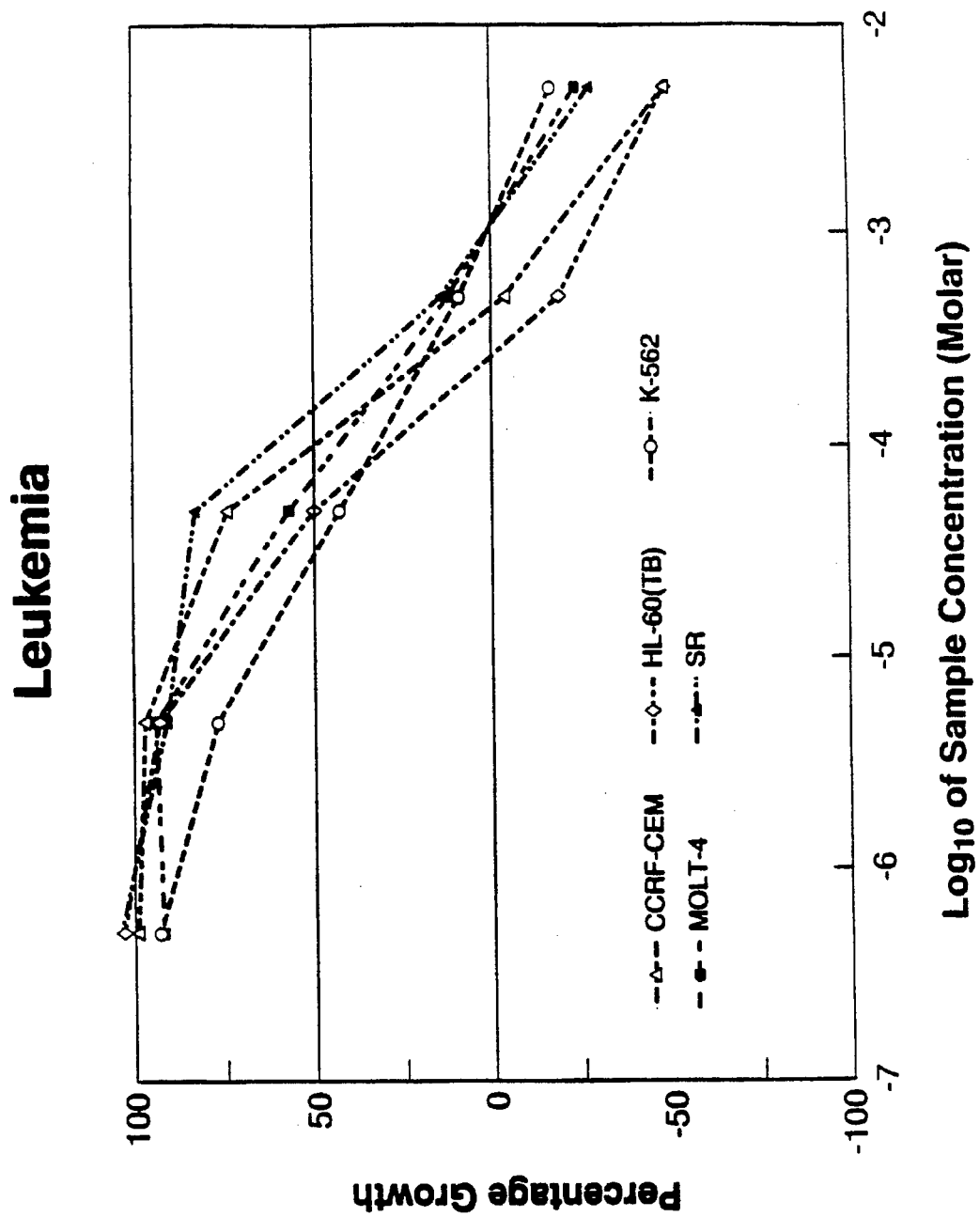
FIG. 5A is particularly relevant to the present invention.
Figure 5C:
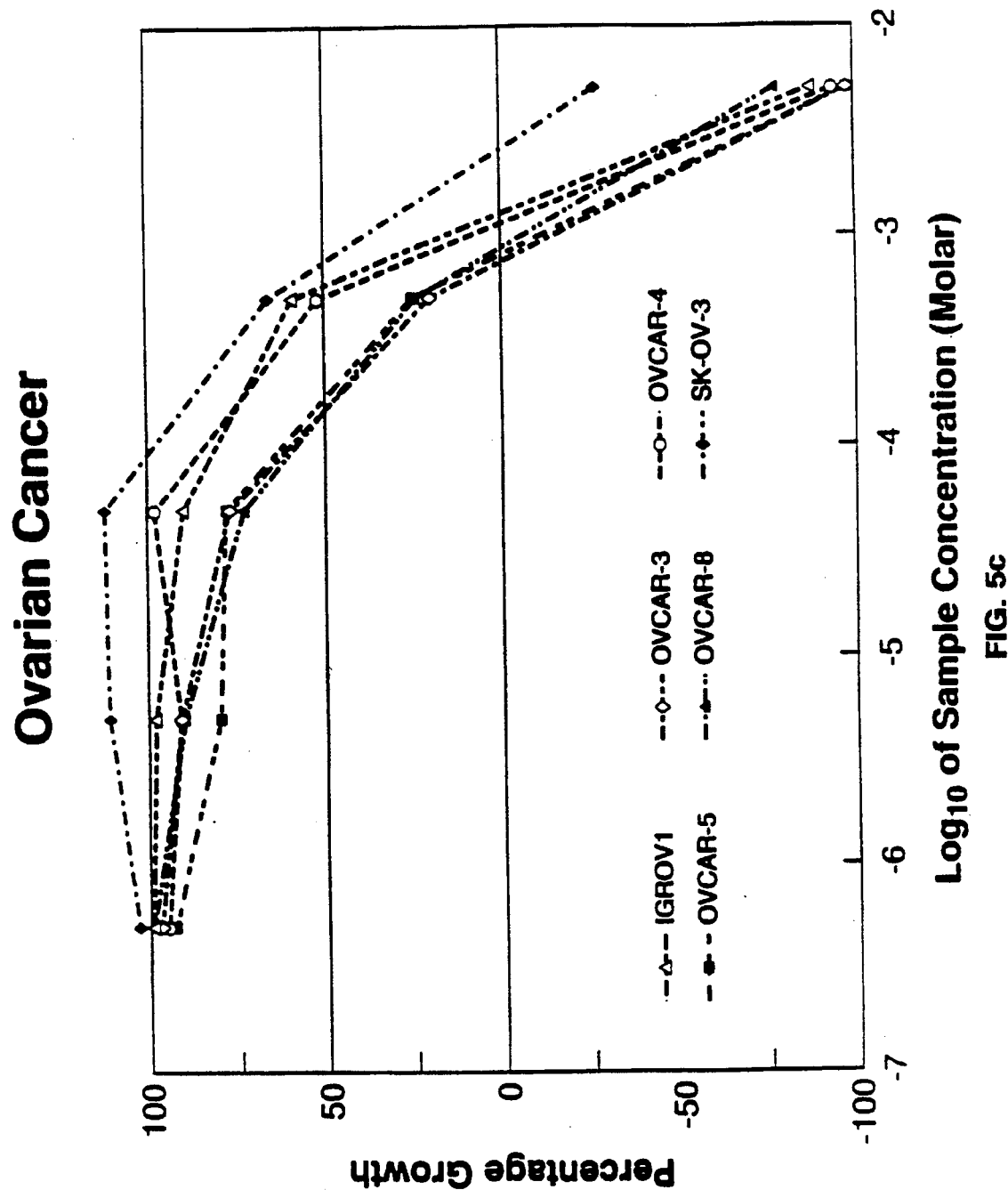
FIG. 5 (A–H) is a set of diagrams demonstrating the effect on percentage growth of a variety of human cancer cell types of various concentrations of perillyl alcohol.
Figure 5D:
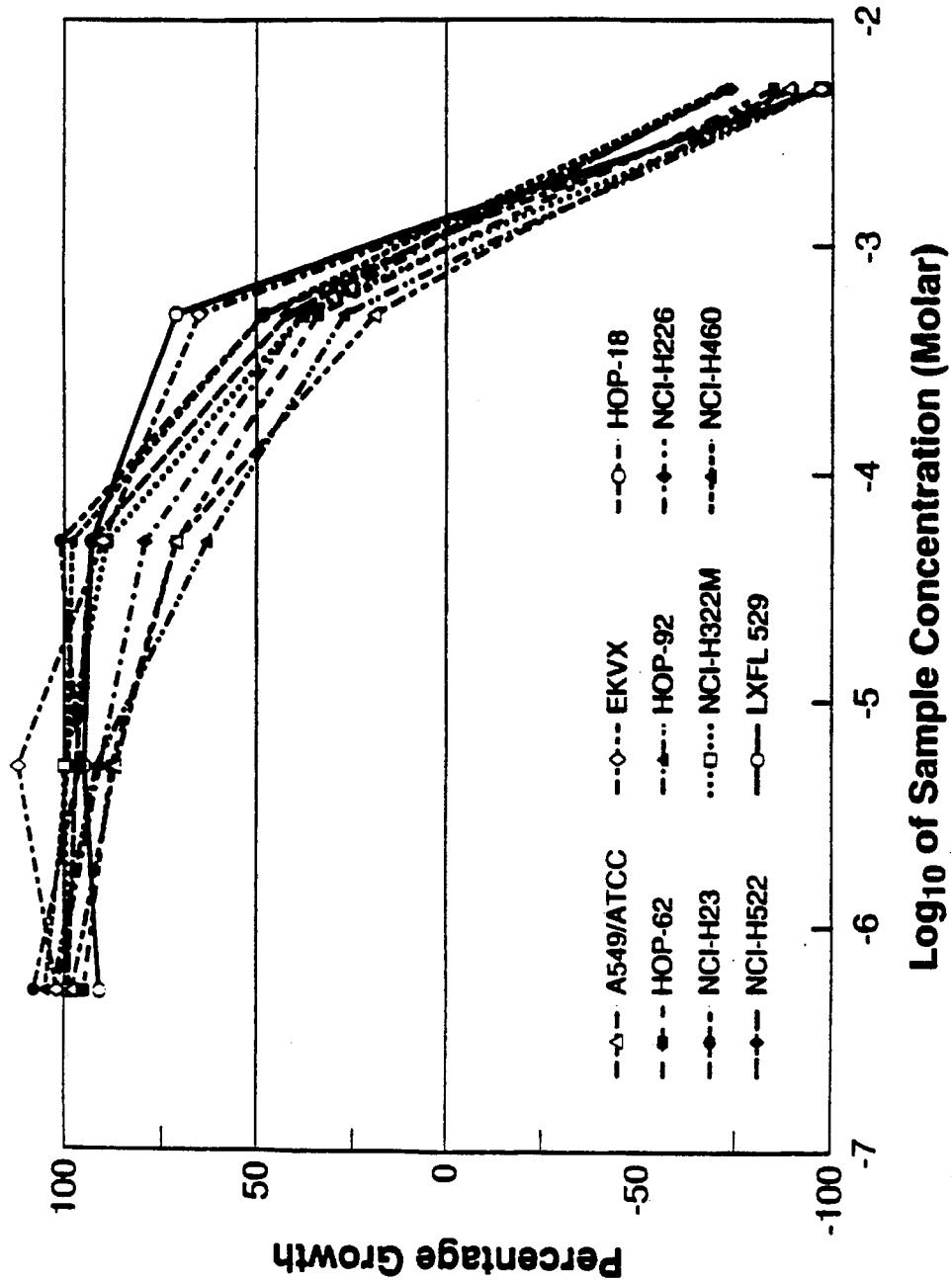
Figure 5E:
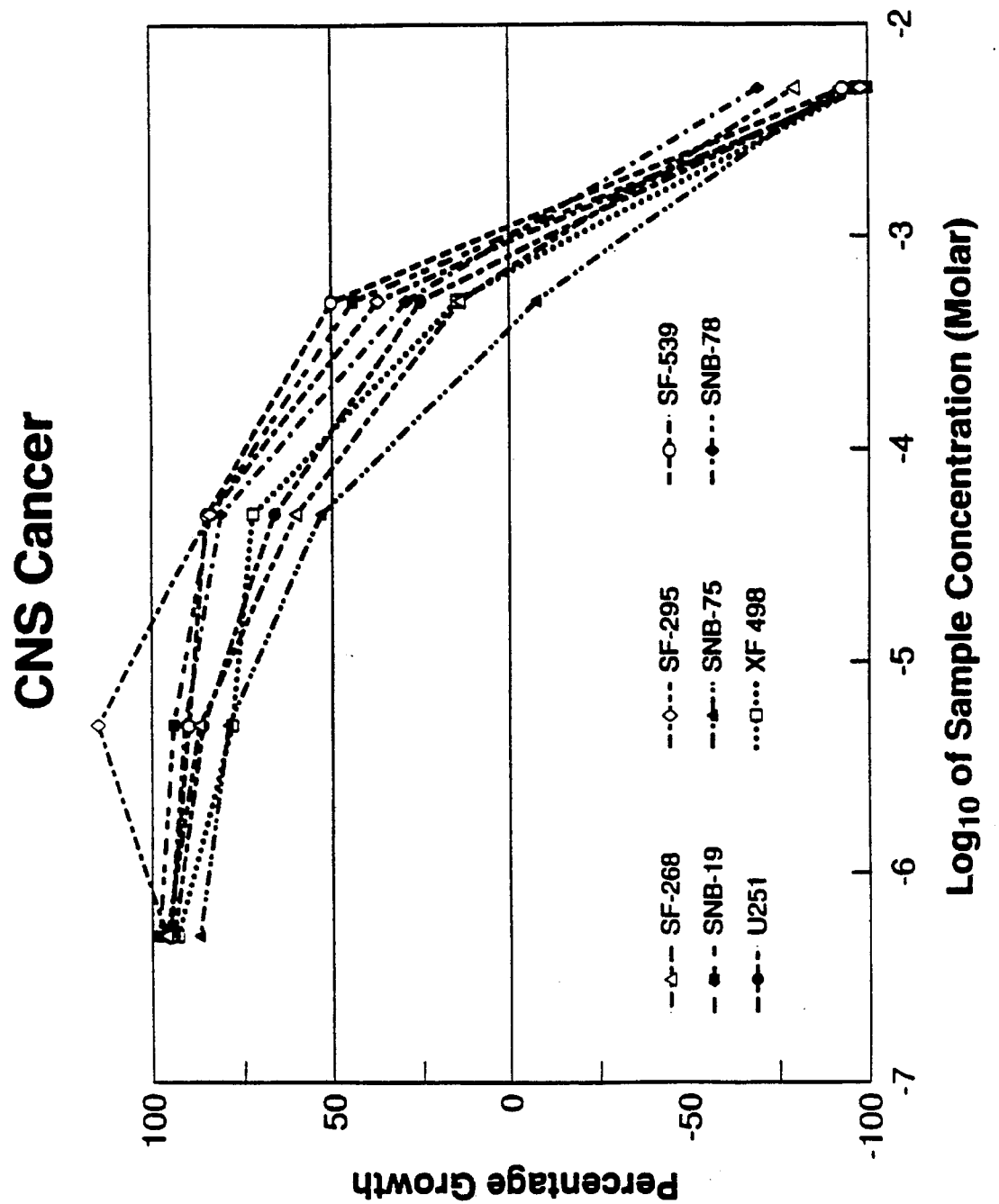
Figure 5F:
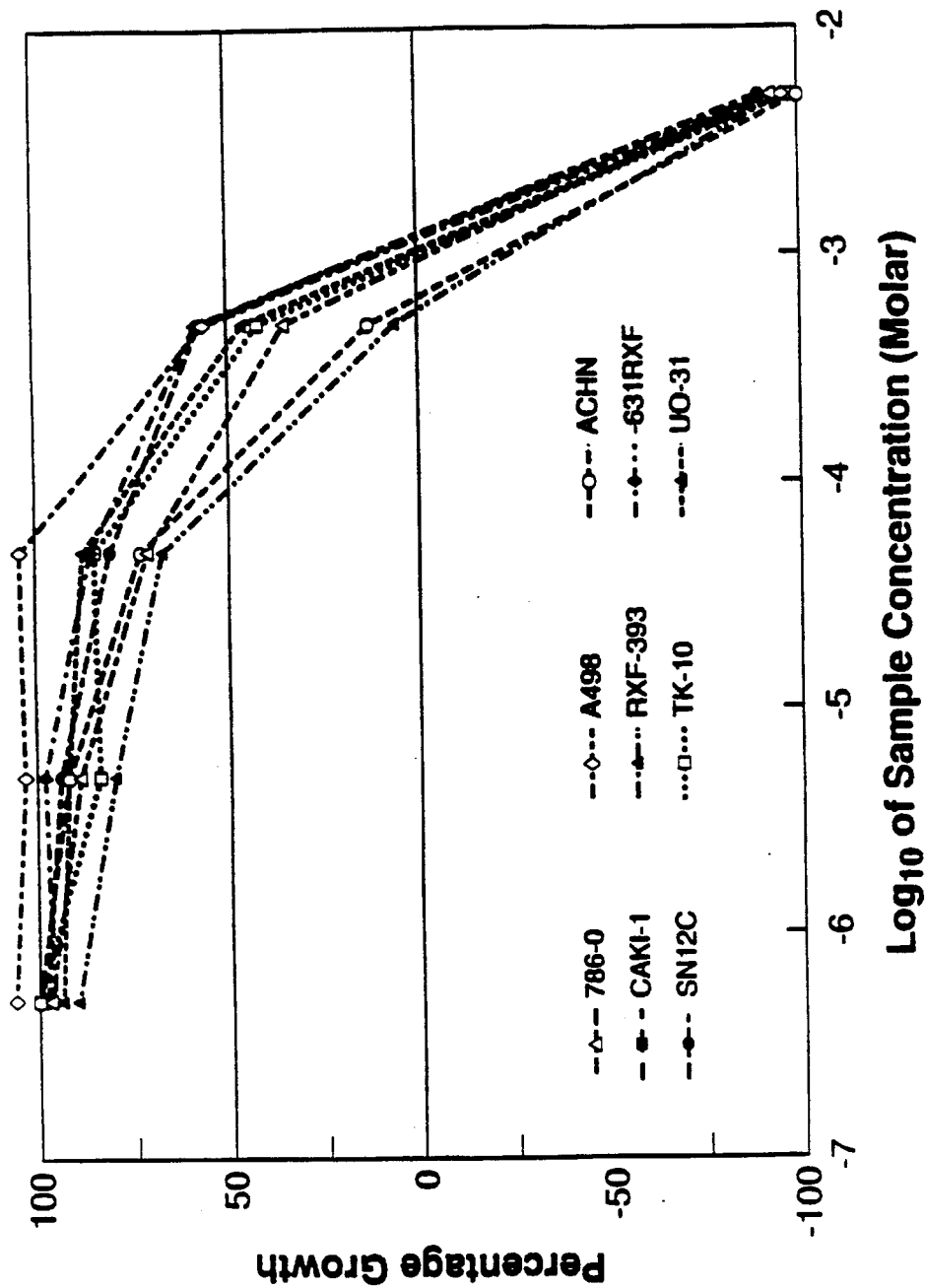
Figure 5G:
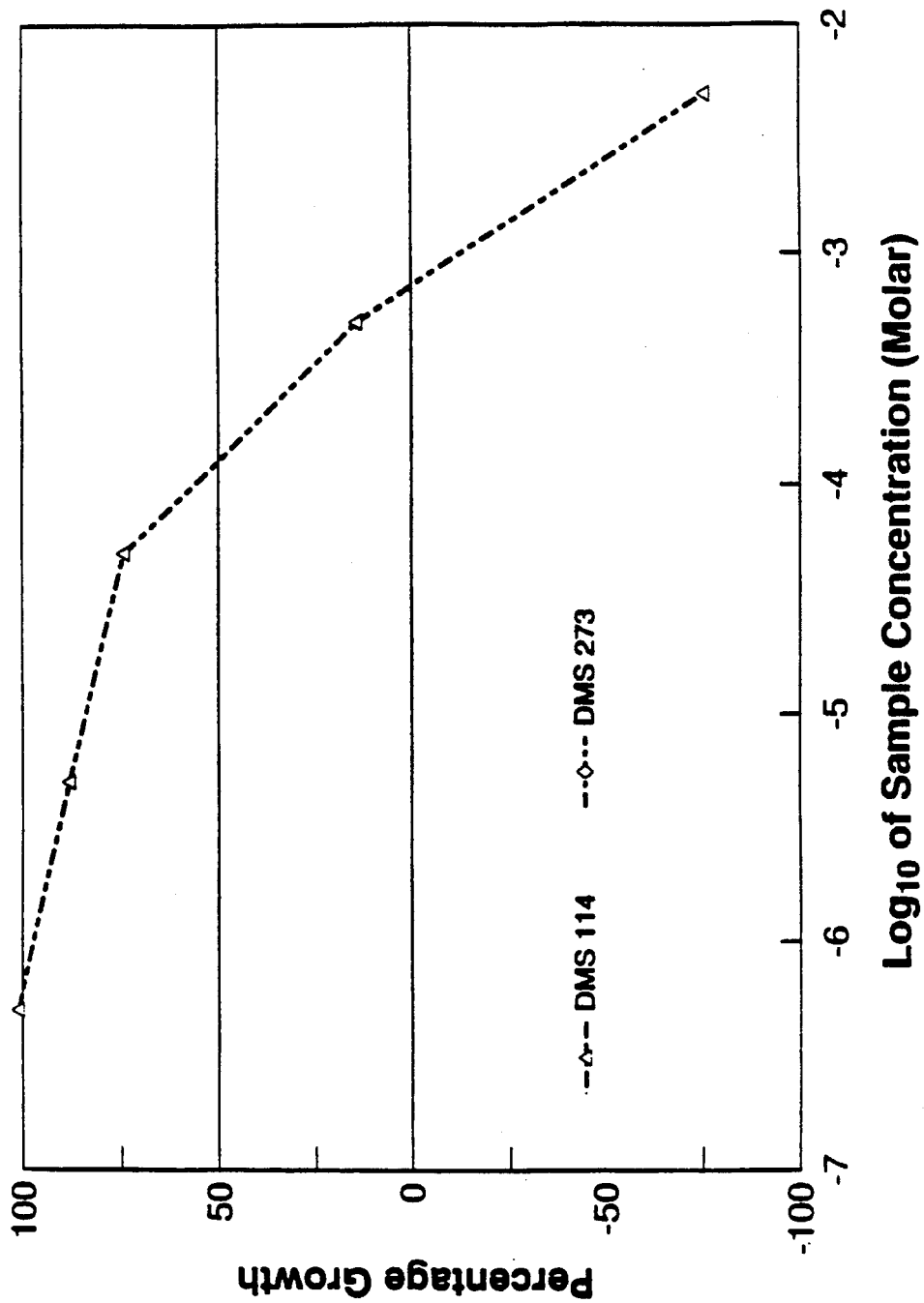
Figure 5H:
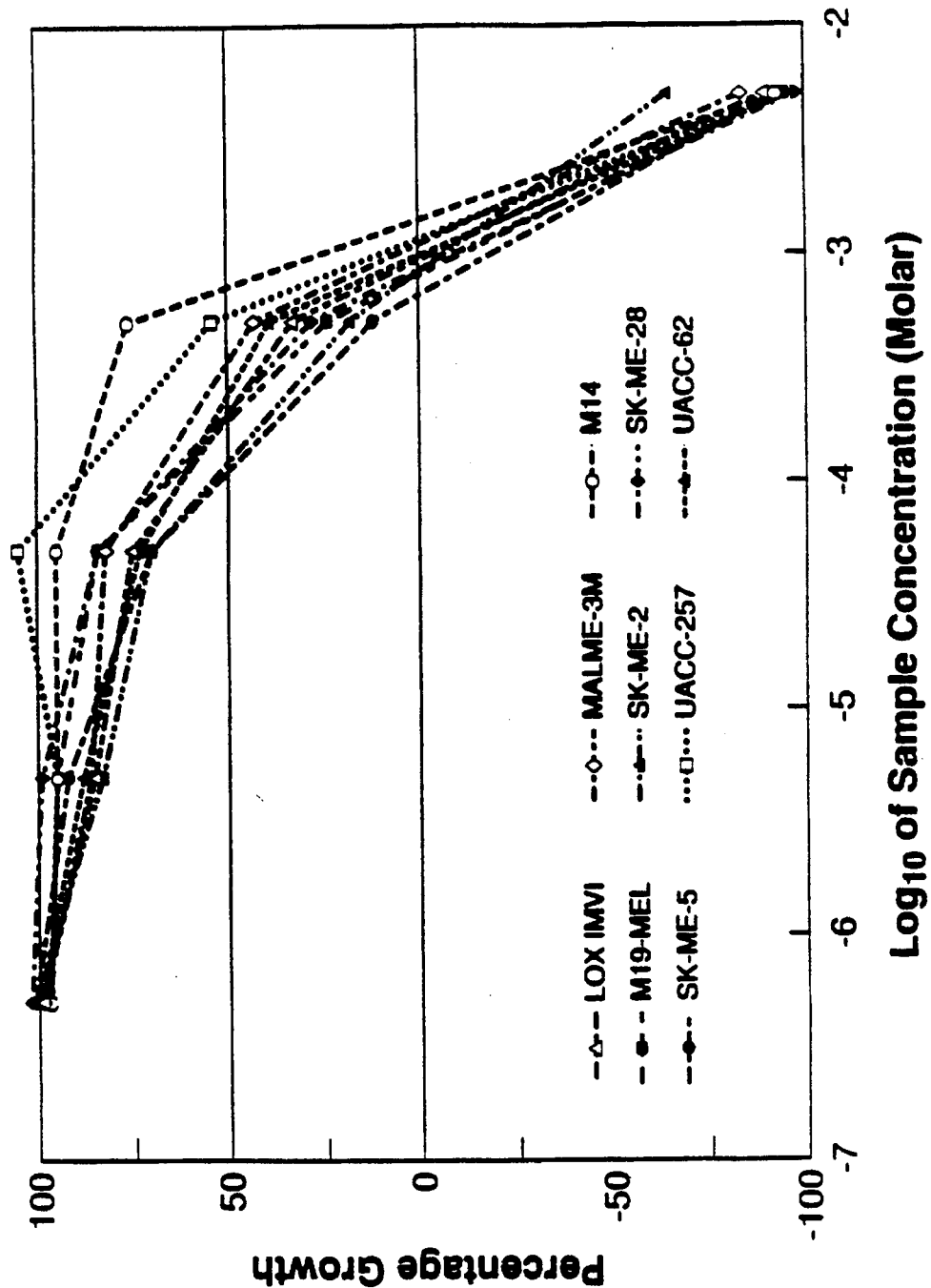

We also have demonstrated differential isoprenylation and inhibition of cell growth in colon adenocarcinoma cells (HT29). Also, FIG. 5A–G demonstrates inhibition of cell growth by perillyl in a variety of human cancer cell types including leukemia cells (FIG. 5A).

b. Appropriate Dose and Administration

In our in vivo tests, we used a perillyl alcohol dose of approximately 2.5 g/kg mammal weight. While this dose might be useful for human treatment, a more conventional treatment dosage would be to calculate the dosage on a surface area basis. Our mammalian in vivo experiment used a surface area dose of approximately 7.5 g/m2. For a human being, this would translate to a dose of approximately 10–15 g/day.

We administered the dose orally. However, other administration modes, such as intravenous administration, would also be appropriate.

Further Leukemia Experiments

4. Use of Perillyl Alcohol to Inhibit Proliferation of bcr/abl Transformed Murine FDC-P1 Myeloid Cells a. Significance Patients with chronic myelogenous leukemia (CML), as well as subgroups of patients with acute lymphoblastic and acute myeloblastic leukemias (ALL and AML, respectively) carry the t(9;22) Philadelphia chromosome (Ph) in their leukemic cells. The Ph translocation fuses the c-abl gene on chromosome 9 to the bcr gene on chromosome 22 which results in expression of a chimeric p210 or p185 bcr/abl protein with constitutive tyrosine kinase activity (S. Clark 40 *Ann. Rev. Med.* 113–122, 1989).

While significant progress has been made in treating many types of leukemias in adults and in children, patients with $Ph^+$ leukemias respond very poorly to conventional therapies. With standard chemotherapy, 80% of children with $Ph^+$ ALL achieve remission, but only 20% remain event-free survivors at 4 years (Crist and Rivera, *Adv. Oncol.* 6: 10–17, 1993). In adults, ALL is generally more difficult to treat than in children and the 20% of these patients that are $Ph^+$ have a dismal prognosis (Schiffer, *Adv. Oncol.* 6: 18–25, 1993). Bone marrow transplantation or, in the case of CML, treatment with alpha interferon provide the only effective cure for some of these patients (Kantarjian, et al., *Blood* 82: 691–703, 1993), but many others either do not response to interferon or are poor candidates for bone marrow transplantation. Furthermore, a significant proportion of patients who initially respond to one of these therapies quickly relapse with an even more aggressive malignancy. Highly sensitive PCR amplification reveals that residual $Ph^+$ leukemia cells frequently survive the induction therapy, and even bone marrow transplantation (Hooberman and Westbrook, *Leuk. Lymphoma* 1: 3–10, 1989).

These observations indicate that a significant fraction of bcr/abl-induced leukemic cells are highly resistant to most therapies and that more effective treatment strategies are needed in order to improve the survival of individuals with bcr/abl-induced leukemia.

b. Effect of Perillyl Alcohol on in vitro Proliferation of bcr/abl-Transformed Myeloid Cells Experiments were designed to test the effects of a range of perillyl alcohol and limonene concentrations (100–800 μM) on bcr/abl-transformed and nontransformed murine FDC-P1 myeloid cells in short-term culture-(FIG. 9). (The p210 bcr/abl oncogene is carried on a helper-free retrovirus referred to as "p210.") FDC-P1 myeloid cells are an immature cell line from myeloid lineage derived from mouse bone marrow (Dexter, TM, *J. Exp. Med.* 152: 1036–1047, 1980).

While the data in FIG. 9A demonstrates that up to 800 μM limonene had no effect on either FDC-P1 transformed or nontransformed FDC-P1 cells, perillyl alcohol was significantly more inhibitory for the growth of p210-transformed FDC-P1 cells compared to nontransformed FDC-P1 cells (FIG. 9B). Thus, 400 μM perillyl alcohol inhibited greater than 80% growth of p210-transformed FDC-P1 cells while inhibiting cell growth in nontransformed cells less than 15%.

Furthermore, when IL-3 was added to the p210-transformed cultures, the growth-inhibitory curve was significantly shifted upward, indicating that adding exogenous growth factor can recover some proliferation and/or viability of the perillyl alcohol-treated p210-transformed cells.

In another experiment, up to 500 μM perillyl alcohol induced only minor changes in the cell cycle distribution of nontransformed cells. However, p210-transformed cells were almost completely arrested at the $G_0/G_1$ stage (Table 3). Furthermore, these cells showed morphological changes suggestive of apoptotic cell death.

Table 3 tabulates the effect of P-OH on cell cycle distribution of nontransformed and p210 transformed FDC-P1 cells.

TABLE 3

| | Cell cycle distribution (% > $G_0/G_1$)[1] | | |
|---|---|---|---|
| | Untreated control | 100 μM P—OH | 500 μM P—OH |
| FDC-P1[2] | 62 | 57 | 49 |
| F-p210.1 | 53 | 53 | 16[3] |

[1]Cells were plated at 2.5 × 10⁵ per ml in duplicate wells of a 24-well plate in the presence of 10% WEHI-3-conditioned media as a source of IL-3 and with the indicated concentration of P—OH. After 24 hours, the cells were fixed in ethanol, permeabilized and stained with propidium iodide, then analyzed for DNA content by flow cytometry. p210-transformed FDC-P1 cells treated with 500 μM P—OH were almost entirely in the $G_0/G_1$ stage of the cell cycle.
[2]FDC-P1 = nontransformed cells, Fp210.1 = 210-transformed FDC-P1 cells.
[3]Significant apoptosis was seen in cells from this group.

It should be noted that pharmacologic analyses revealed that rats fed 2% perillyl alcohol attain a serum concentration of perillyl alcohol and some of its serum metabolites within the effective concentration range observed in these in vitro experiments. In sum, these results indicate that perillyl alcohol reverts autonomously growing malignant cells to a factor-dependent, apoptosis-sensitive state. In light of these observations, and our belief that $p21^{ras}$ may be a target for perillyl alcohol activity in bcr/abl-transformed cells, it may be relevant that cellular ras activity is required for proliferating cells to pass through $G_1$ (Dobrowski, et al., *Mol. Cell Biol.* 14: 5441–49, 1994).

5. Effects of Perillyl Alcohol on bcr/abl-Induced Leukemia in Mice

Experiments were done in which the non-malignant mouse bone marrow cell line, FDC-P1, was transformed with a retrovirus engineered to express the p210 bcr/abl oncogene. As described above, the bcr/abl oncogene plays a major role in the development of human Philadelphia chromosome (Ph) positive leukemias. Therefore, this mouse system represents a model of Ph⁺ human leukemia. Injection of syngeneic animals with the bcr/abl transformed FDC-P1 cells induces lethal hematopoietic malignancy in which all animals had died within 30 days post-injection (absent perillyl alcohol).

Animals were fed either a control diet or a diet containing 2% perillyl alcohol and were challenged with either 3×10⁵ or 3×10⁶ bcr/abl-transformed cells. All animals on the control diet died by day 26.

It appeared that most mice resisted the perillyl alcohol diet and went on a fast to avoid it. Even with limited dosages being ingested, we observed that about 20% of the animals on the perillyl alcohol diet survived 10 to 15 days longer than control animals. (This direct avoidance should not be a problem for humans.) We are now examining alternative ways to expose the mice to perillyl alcohol (e.g. injection).

We claim:

1. A method for causing the regression of a leukemia cell malignancy, comprising the step of administering to a leukemia cell malignancy-containing mammal an effective amount of perillyl alcohol.

2. The method of claim 1, wherein the leukemia cell malignancy is a Ph⁺ leukemia.

3. A method for causing the regression of a leukemia cell malignancy, comprising the step of administering to a mammalian leukemia cell malignancy an effective amount of perillyl alcohol.

* * * * *